(12) United States Patent
Seegert et al.

(10) Patent No.: US 9,408,750 B2
(45) Date of Patent: Aug. 9, 2016

(54) REDUCED-PRESSURE TREATMENT SYSTEMS AND METHODS EMPLOYING DEBRIDEMENT MECHANISMS

(75) Inventors: Charles Alan Seegert, North Richland, TX (US); Robert Peyton Wilkes, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 1052 days.

(21) Appl. No.: 13/462,817

(22) Filed: May 3, 2012

(65) Prior Publication Data

US 2012/0220924 A1 Aug. 30, 2012

Related U.S. Application Data

(63) Continuation of application No. 12/639,351, filed on Dec. 16, 2009, now Pat. No. 8,486,032.

(60) Provisional application No. 61/140,654, filed on Dec. 24, 2008.

(51) Int. Cl.
*A61M 37/00* (2006.01)
*B23P 17/04* (2006.01)
(Continued)

(52) U.S. Cl.
CPC .......... *A61F 13/00068* (2013.01); *A61B 17/32* (2013.01); *A61F 13/00063* (2013.01);
(Continued)

(58) Field of Classification Search
CPC .............................. A61M 37/00; B23P 17/04
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Philip R Wiest
*Assistant Examiner* — Sara Sass

(57) ABSTRACT

Reduced-pressure treatment systems and methods are disclosed that employ debridement mechanisms to remove unwanted tissue. In one instance, a reduced-pressure treatment system for treating a tissue site on a patient includes a manifold member for distributing reduced pressure to the tissue site, a support member for disposing proximate the tissue site and the manifold, and a debridement mechanism coupled to the support member. The debridement mechanism is for debriding the tissue site. The system further includes a sealing drape for placing over the tissue site and manifold member. The sealing drape is operable to form a fluid seal over the tissue site and manifold member. The system also includes a reduced-pressure subsystem for delivering a reduced pressure to the sealing drape. The system may further include a chemical-debridement subsystem. Other systems, manifolds, and methods are disclosed.

17 Claims, 5 Drawing Sheets

(51) Int. Cl.
*A61M 27/00* (2006.01)
*A61F 13/00* (2006.01)
*A61B 17/32* (2006.01)
*A61M 1/00* (2006.01)
*A61B 17/30* (2006.01)
*A61B 17/00* (2006.01)

(52) U.S. Cl.
CPC ........... *A61M1/0084* (2013.01); *A61M 1/0088* (2013.01); *A61M 27/00* (2013.01); *A61B 17/30* (2013.01); *A61B 2017/00561* (2013.01); *Y10T 29/49826* (2015.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,881,550 A | 11/1989 | Kothe | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,697,920 A | 12/1997 | Gibbons | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,375,634 B1 | 4/2002 | Carroll | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,486,032 B2 * | 7/2013 | Seegert et al. | 604/313 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0124199 A1 * | 7/2003 | Nietsch et al. | 424/538 |
| 2004/0228694 A1 * | 11/2004 | Webb | B23B 27/145 407/113 |
| 2005/0228329 A1 * | 10/2005 | Boehringer et al. | 602/52 |
| 2006/0287667 A1 * | 12/2006 | Abela | A61B 17/320758 606/200 |
| 2007/0239078 A1 * | 10/2007 | Jaeb | 601/2 |
| 2009/0182362 A1 * | 7/2009 | Thompson | A61B 17/320758 606/159 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |

(56) References Cited

FOREIGN PATENT DOCUMENTS

| WO | 90/10424 | 9/1990 |
|---|---|---|
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Đukić, Ž. Maksimović, Đ.. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

\* cited by examiner

REDUCED-PRESSURE TREATMENT SYSTEMS AND METHODS EMPLOYING DEBRIDEMENT MECHANISMS

RELATED APPLICATIONS

The present application is a continuation of U.S. patent application Ser. No. 12/639,351, entitled "Reduced-Pressure Treatment Systems and Methods Employing Debridement Mechanisms," filed on 16 Dec. 2009, now U.S. Pat. No. 8,486,032, which is incorporated herein by reference for all purposes, and which claims the benefit, under 35 U.S.C. §119(e), of the filing of U.S. Provisional Patent Application Ser. No. 61/140,654, entitled "Reduced-Pressure Treatment Systems and Methods Employing Debridement Mechanisms," filed 24 Dec. 2008, which is incorporated herein by reference for all purposes.

BACKGROUND

Wounds frequently require debridement, or removal of undesirable tissue, to promote healing. Most debridement techniques suffer from a lack of specificity to the undesirable tissue. Therefore, healthy tissue may be removed along with the undesirable tissue, which frequently leads to longer healing times as well as discomfort and pain to the patient.

Maggot debridement therapy has long been noted for its ability to debride a wound such that undesirable tissue, such as necrotic tissue, is generally removed from the wound while leaving healthy tissue in tact. While maggot therapy may be useful for debriding a wound, it is a costly and time consuming procedure. Additionally, maggot therapy is labor intensive and is frequently objectionable to both health care providers and patients alike. Other shortcomings exist as well.

SUMMARY

Shortcomings with wound care systems and methods are addressed by the illustrative, non-limiting embodiments herein. According to one illustrative, non-limiting embodiment, a reduced-pressure treatment system for treating a tissue site on a patient includes a manifold member for distributing reduced pressure to the tissue site, a support member for disposing proximate the tissue site and the manifold, and a debridement mechanism coupled to the support member. The debridement mechanism is for debriding the tissue site. The system further includes a sealing drape for placing over the tissue site and manifold member. The sealing drape is operable to form a fluid seal over the tissue site and manifold member. The system also includes a reduced-pressure subsystem for delivering a reduced pressure to the sealing drape. The system may further include a chemical-debridement subsystem.

A manifold member for treating a tissue site on a patient includes a manifold material for distributing reduced pressure, a support member associated with the manifold material, and a debridement mechanism for debriding the tissue site. The debridement mechanism is coupled to the support member.

A method for treating a tissue site on a patient includes placing a manifold member proximate the tissue site. The manifold member includes a debridement mechanism for debriding the tissue site. The method further includes disposing a sealing drape over the manifold member and the patient's epidermis, forming a fluid seal between the sealing drape and the patient's epidermis, and providing a reduced pressure to the manifold member. When reduced pressure is applied, the debridement mechanism debrides the tissue site.

A method of manufacturing a manifold member for treating a tissue site on a patient includes forming a manifold member for placing over a tissue site. The manifold member includes a support member. The method further includes coupling a debridement mechanism to the support member. The debridement mechanism is configured to debride a tissue site under the influence of reduced pressure.

Other features and advantages of the illustrative, non-limiting embodiments will become apparent with reference to the drawings and detailed description that follow.

BRIEF DESCRIPTION OF THE DRAWINGS

A more complete understanding may be obtained by reference to the following Detailed Description when taken in conjunction with the accompanying Drawings, wherein like numerals indicate like elements throughout, and wherein.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative, non-limiting embodiments are defined only by the appended claims.

Figure 1:
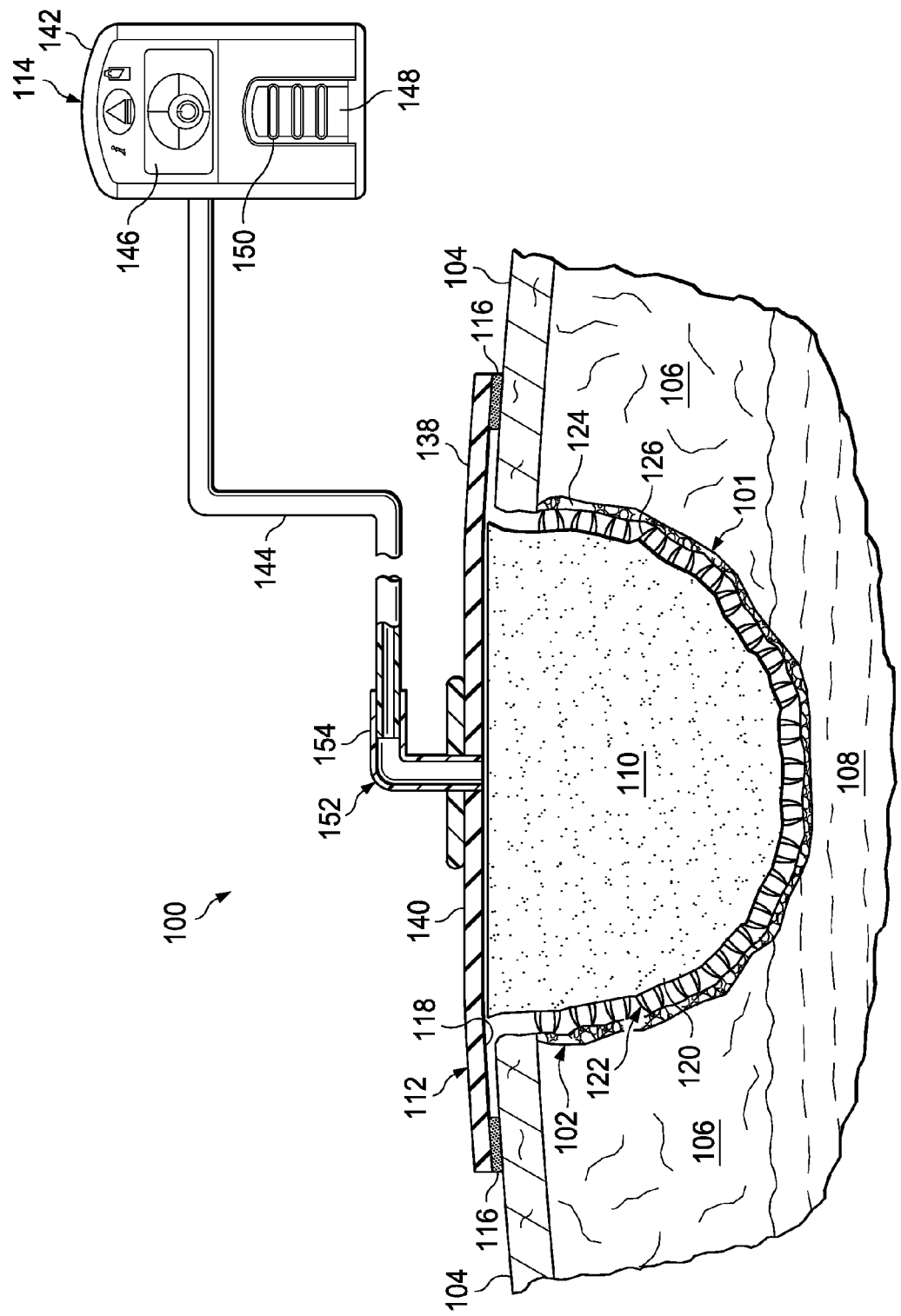
FIG. 1 is a schematic, diagram with a portion shown in cross section of an illustrative, non-limiting embodiment of a reduced-pressure treatment system employing a debridement mechanism.
Figure 2A:
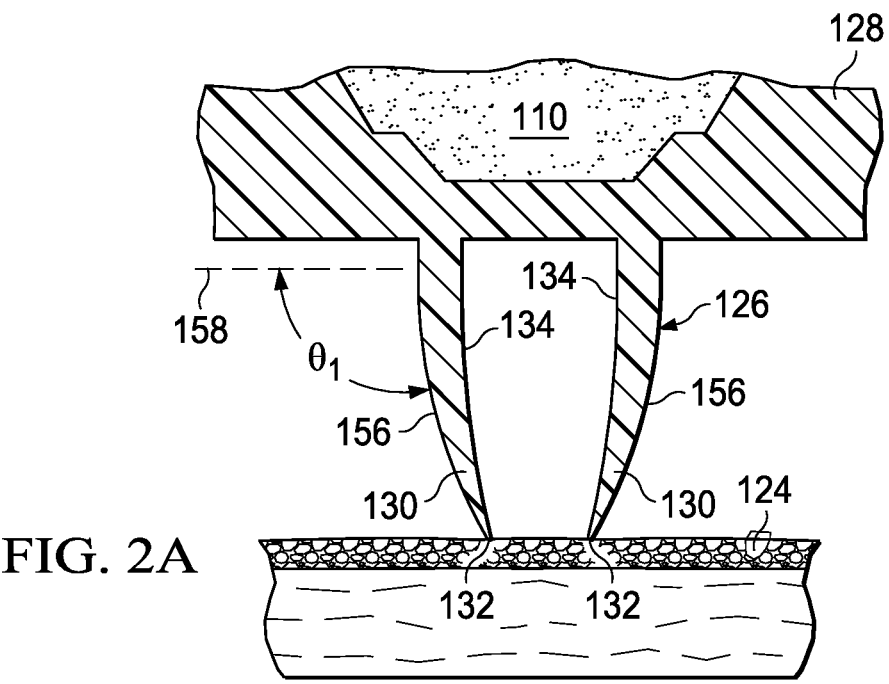
FIG. 2A is a schematic, cross-sectional view of a pincer, which is shown in an open position, from the reduced-pressure treatment system of FIG. 1.
Figure 2B:
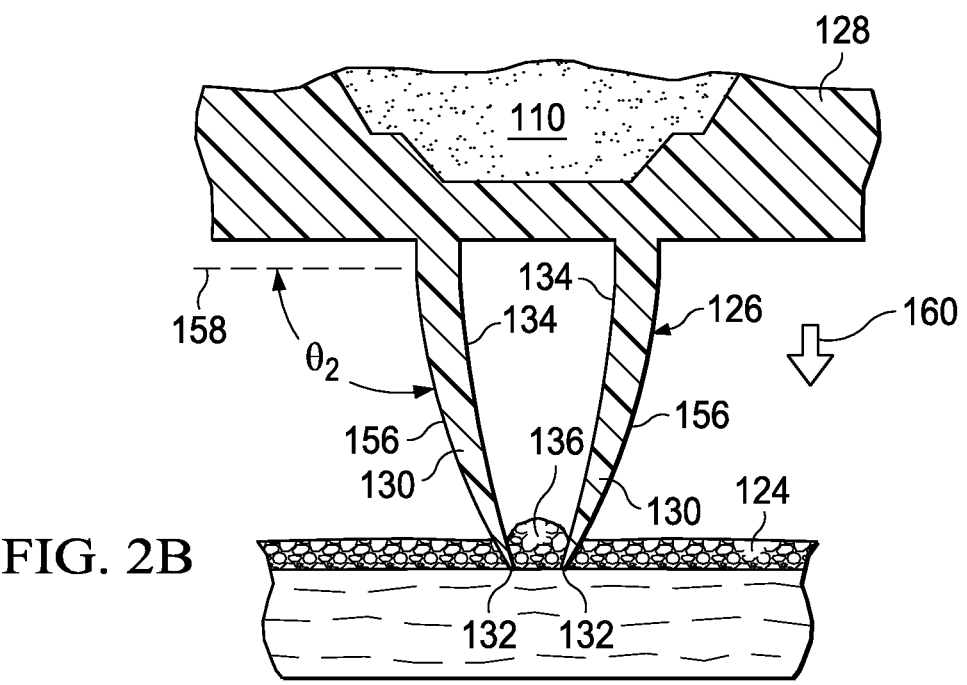
FIG. 2B is a schematic, cross-sectional view of the pincer of FIG. 2A shown after initiation of reduced pressure.
Figure 2C:
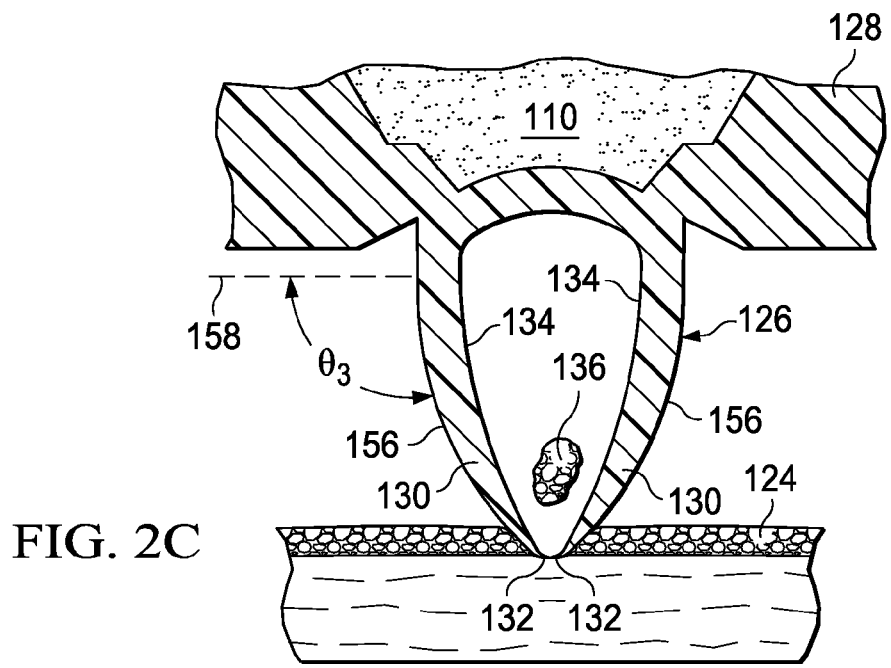
FIG. 2C is a schematic, cross-sectional view of the pincer of FIG. 2A shown in a closed position.

Referring now primarily to FIG. 1-2C, a reduced-pressure treatment system 100 for treating a tissue site 101, e.g., a wound 102, is presented. The wound 102 may include, without limitation, any irregularity with a tissue, such as an open wound, surgical incision, or diseased tissue. The reduced-pressure treatment system 100 is presented in the context of a general tissue site 101 that includes the wound 102, which is through the epidermis 104, or generally skin, and the dermis 106 and reaching into a hypodermis, or subcutaneous tissue 108. The reduced-pressure treatment system 100 may be used to treat a wound of any depth, as well as many different types of wounds including open wounds or other tissue sites. The tissue site 101 may be the bodily tissue of any human, animal, or other organism, including bone tissue, adipose tissue, muscle tissue, dermal tissue, vascular tissue, connective tissue, cartilage, tendons, ligaments, or any other tissue. Unless otherwise indicated, as used herein, "or" does not require mutual exclusivity. The wound 102 may include a layer of necrotic tissue 124. In at least some instances, it may be desirable to remove the necrotic tissue 124 in order to promote healing of the wound 102. While the illustrative, non-limiting embodiment shows the reduced-pressure treatment system 100 in the context of the wound 102 having a layer of necrotic tissue 124 therein, it will be appreciated that the reduced-pressure treatment system 100 may be used with any tissue site having undesirable tissue, such as, eschar, necrotic, damaged, infected, contaminated, or adherent tissue, or foreign material therein.

The reduced-pressure treatment system 100 includes a manifold member 110, a sealing drape 112, and a reduced-pressure subsystem 114. The reduced-pressure treatment system 100 may also include an attachment device 116. The manifold member 110 is positionable between a tissue-facing surface 118 of the sealing drape 112 and the tissue site 101.

The term "manifold" as used herein generally refers to a substance or structure that is provided to assist in applying reduced pressure to, delivering fluids to, or removing fluids from a tissue site, e.g., the wound 102. The manifold member 110 typically includes a plurality of flow channels or pathways that are interconnected to improve distribution of fluids provided to and removed from around the manifold member 110. The manifold member 110 may be a biocompatible material that is capable of being placed in contact with tissue site, e.g., wound 102, and distributing reduced pressure to the tissue site 101. Examples of manifold members 110 may include, for example, without limitation, devices that have structural elements arranged to form flow channels, such as, for example, cellular foam, open-cell foam, porous tissue collections, liquids, gels, and foams that include, or cure to include, flow channels. The manifold member 110 may be porous and may be made from foam, gauze, felted mat, etc. The manifold member 110 may be formed from a porous material, e.g., a foam, or from a material that is made porous, e.g., a solid member in which apertures have been applied. In one illustrative, non-limiting embodiment, the manifold member 110 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. Other embodiments might include "closed cells." In some situations, the manifold member 110 may also be used to distribute fluids such as medications, antibacterials, growth factors, and various solutions to the tissue site. Other layers may be included in or on the manifold member 110, such as absorptive materials, wicking materials, hydrophobic materials, and hydrophilic materials.

A tissue-facing surface 120 of the manifold member 110 includes one or more debridement mechanisms 122 for debriding the tissue site 101, e.g., the wound 102. As used herein, the terms "debride," "debriding," and "debridement," relate to the act of removing or the removal of undesirable tissue, such as, eschar, necrotic, damaged, infected, contaminated, or adherent tissue, or foreign material from a tissue site. In the illustrative, non-limiting embodiment, each debridement mechanism 122 is operable to remove necrotic tissue 124 from the wound 102. However, it will be appreciated that each debridement mechanism 122 may be operable to remove any suitable type of undesirable tissue or foreign material from any suitable tissue site. In one embodiment, the debridement mechanism 122 is configured to allow the manifold member 110 to induce microstrain at the tissue site 101, e.g., within the wound 102. In another embodiment, the debridement mechanism 122 and the manifold member 110 are both operable to induce microstrain at the tissue site 101, e.g., within the wound 102.

The debridement mechanism 122 may be coupled to the manifold member 110. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, mechanical, thermal, or electrical coupling. Fluidly coupling means that fluid is in communication between the designated parts or locations. Alternatively, the debridement mechanism 122 may be associated proximate manifold member 110 without coupling.

In the illustrative, non-limiting embodiment, and as clearly shown in FIGS. 2A-2C, each debridement mechanism 122 may be a pincer 126. In one embodiment, a plurality of pincers 126 are arranged in an array over the tissue-facing surface 120 of the manifold member 110. However, it will be appreciated that any number of pincers 126 may be employed. The pincers 126 may be arranged in a pattern or randomly.

Figure 3:
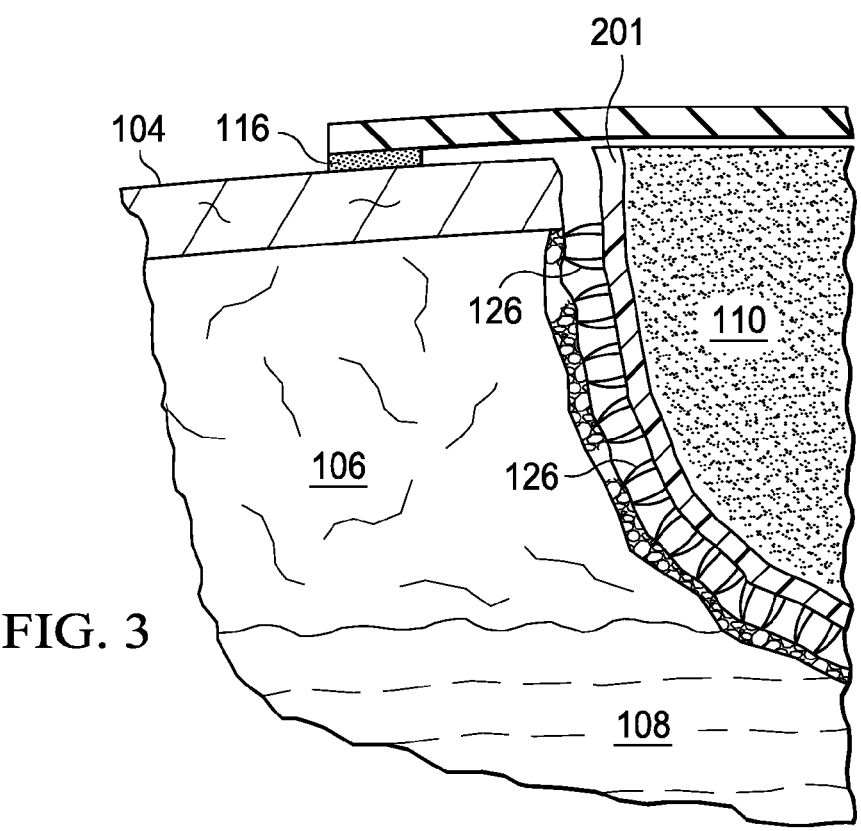
FIG. 3 is a schematic, cross-sectional view of an alternative embodiment of a portion of a reduced-pressure treatment system employing a debridement mechanism.

Each pincer 126 is typically a molded component of the manifold member 110, but it will be appreciated that each pincer 126 may be a separate component that is otherwise associated or coupled to the manifold member 110. In an alternative embodiment, as shown in FIG. 3, each pincer 126 may be a molded component of, or otherwise coupled to, a secondary manifold 201 that may be coupled to or associated with the manifold member 110. The secondary manifold 201 may be similar in structure to the manifold member 110, or may otherwise include one or more apertures (not shown) between or adjacent to one or more pincer blades 130 so that the secondary manifold 201 does not interfere with the previously described function of the manifold member 110. In still another illustrative, non-limiting embodiment, the debridement mechanism includes a first jaw member coupled to the support member 128; a second jaw member coupled to the support member 128 and spaced from the first jaw member; and wherein the first jaw member and second jaw member are operable to move from a first, open position to a second, biting position under the influence of reduced pressure.

Referring again primarily to FIGS. 2A-2C, each pincer 126 includes a support member 128 coupled to the manifold member 110. A pair of pincer blades 130 extends from the support member 128. While the illustrative, non-limiting embodiment shows each pincer blade 130 as extending substantially normal from the support member 128, it will be appreciated that each pincer blade 130 may extend from the support member 128 at any suitable angle. Each pincer blade 130 is shaped so that the pincer blade 130 tapers to a point 132; however, it will be appreciated that each pincer blade 130 may have any suitable shape. Furthermore, while the illustrative, non-limiting embodiment shows the pincer 126 as having a pair of pincer blades 130, it will be appreciated that the pincer 126 may have any suitable number of pincer blades 130. As will be discussed further below, the pincer 126 is configured such that, under the influence of reduced pressure, the pincer 126 will move from an open position (FIG. 2A) to a closed position whereby a portion 136 of necrotic tissue 124 is removed from the wound 102 (FIG. 2C). In moving from the open position to the closed position, the pincer 126 digs into, or scrapes, a portion 136 of the neurotic tissue 124 from the wound 102 (See FIG. 2B). In an another embodiment, after the pincers 126 have moved to a closed position and under the continued influence of reduced pressure, the pincer blades 130 may move from a closed position to a collapsed position whereby the inner surface 134 of each pincer blade 130 confronts or approaches the tissue-facing surface 120 of the manifold member 110.

Referring again primarily to FIG. 1, the sealing drape 112 includes a first surface 140 and the tissue-facing surface 118. The sealing drape 112 may be sized so that the sealing drape 112 overlaps the wound 102 in such a manner that a drape extension 138 extends beyond the periphery of the wound 102. The sealing drape 112 may be any material that provides a fluid seal. "Fluid seal," or "seal," means a seal adequate to maintain reduced pressure at a desired site given the particular reduced-pressure source or subsystem involved. The sealing drape 112 may, for example, be an impermeable or semi-permeable, elastomeric material that has pore sizes less than about 20 microns. "Elastomeric" means having the properties of an elastomer. It generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Additional, specific examples of sealing member materials include a silicone drape, 3M Tegaderm® drape, acrylic drape such as one available from Avery Dennison, or an incise drape.

An attachment device 116 may be used to hold the sealing drape 112 against the patient's epidermis 104 or another layer, such as a gasket or additional sealing member. The attachment device 116 may take numerous forms. For example, the attachment device 116 may be a medically-acceptable, pressure-sensitive adhesive that extends about one or more drape extensions 138 of the sealing drape 112. Alternatively, the pressure-sensitive adhesive may span the entire width of the sealing drape 112. Alternative attachment devices may include, but are not limited to, heat-activated adhesives, sealing tapes, double-sided sealing tapes, pastes, hydrocolloids, hydrogels, hooks, sutures, etc.

The reduced-pressure subsystem 114 includes a reduced-pressure source 142, which can take many different forms. The reduced-pressure source 142 provides reduced pressure as a part of the reduced-pressure treatment system 100. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the manifold member 110, a reduced-pressure conduit 144, or conduit 144, and proximate the tissue site 101, e.g., wound 102. As the hydrostatic pressure around the tissue site 101, e.g., wound 102, approaches the desired reduced pressure, the flow may subside, and the reduced pressure may be maintained. Unless otherwise indicated, values of pressure stated herein are gauge pressures. The reduced pressure delivered may be static, dynamic (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The reduced-pressure subsystem 114 provides reduced pressure. The reduced-pressure subsystem 114 includes the reduced-pressure source 142 that may be any means of supplying a reduced pressure, such as a vacuum pump or wall suction. While the amount and nature of reduced pressure applied to a tissue site will typically vary according to the application, the reduced pressure will typically be between −5 mm Hg and −500 mm Hg.

In the illustrative, non-limiting embodiment, the reduced-pressure source 142 has a battery compartment 146 and a canister region 148 with windows 150 providing a visual indication of the level of fluid within canister 148. An interposed membrane filter, such as hydrophobic or oleophobic filter, might be interspersed between reduced-pressure conduit 144 and the reduced-pressure source 142.

The reduced pressure provided by the reduced-pressure source 142 is delivered through the reduced-pressure conduit 144 to a reduced-pressure interface 152, or interface 152, which may be an elbow port 154. In one illustrative, non-limiting embodiment, the elbow port 154 is a TRAC® technology port available from Kinetic Concepts, Inc. of San Antonio, Tex. The reduced-pressure interface 152 allows the reduced pressure to be delivered to the sealing drape 112 and realized within an interior portion of sealing drape 112 and the manifold member 110. In this illustrative, non-limiting embodiment, the elbow port 154 extends through the sealing drape 112 to the manifold member 110, but numerous arrangements are possible.

In operation, the manifold member 110 may be placed proximate the tissue site 101, e.g., wound 102. The manifold member 110 may be placed within the wound 102, or may overlay a portion of the wound 102. As clearly shown in FIG. 2A, when the manifold member 110 is initially placed in the wound 102, each pincer 126 is in an open position whereby the points 132 of two or more corresponding pincer blades 130 are in spaced relationship relative to one another. Additionally, the point 132 of each pincer blade 130 abuts a portion of tissue within the wound 102 and preferably abuts necrotic tissue 124. In the illustrative, non-limiting embodiment, the initial angle ($\theta_1$) between the outer surface 156 of each pincer blade 130 and a horizontal (for the orientation shown) reference line 158 is between 70 and 110 degrees and more particularly between 80 and 100 degrees and still more particularly between 85 and 95 degrees. In one particular illustrative, non-limiting embodiment, the initial angle is approximately 90 degrees (90°). It will, however, be appreciated that the initial angle ($\theta_1$) may be any suitable angle.

The sealing drape 112 may be placed over the manifold member 110 such that the drape extension 138 extends beyond the periphery of the wound 102. The drape extension 138 may be secured to the patient's epidermis 104 by the attachment device 116 in order to form a fluid seal between the patient's epidermis 104 and the sealing drape 112. The reduced-pressure interface 152 may then be applied, if not already installed, and the reduced-pressure conduit 144 fluidly coupled to the reduced-pressure interface 152. The reduced-pressure conduit 144 is fluidly coupled to the reduced-pressure source 142. The reduced-pressure source 142 may then be activated such that a reduced pressure is delivered to the interior of the sealing drape 112 and manifold member 110.

As the reduced pressure is delivered, the manifold member 110 may contract to form a semi-rigid substrate. As reduced pressure is delivered and the manifold member 110 begins to contract, a compressive force develops, in the direction represented by force vector 160, which begins to drive the points 132 of each pincer blade 130 into the necrotic tissue 124. Additionally, as shown in FIG. 2B, the points 132 of two or more corresponding pincer blades 130 begin to be forced together whereby a portion 136 of necrotic tissue 124 is received between the corresponding pincer blades 130. In the illustrative, non-limiting embodiment, when the points 132 of two or more corresponding pincer blades 130 begin to be forced together, the angle ($\theta_2$) between the outer surface 156 of each pincer blade 130 and the horizontal reference line 158 is typically more than the initial angle ($\theta_2 > \theta_1$).

As shown in FIG. 2C, with continued delivery of reduced pressure and continued contraction of the manifold member 110, each pincer 126 may be moved to a closed position wherein the points 132 of the corresponding pincers blades 130 are forced even closer together whereby the portion 136 of necrotic tissue 124 therebetween is removed from the wound 102. In the illustrative, non-limiting embodiment, when a pincer 126 is moved to a closed position, the angle ($\theta_3$) between the outer surface 156 of each pincer blade 130 and the horizontal reference line 158 is more than the angle when the pincer blades 130 begin to be forced together (i.e., $\theta_2$), as well as less than the initial angle ($\theta_3 > \theta_2 > \theta_1$). The reduced pressure delivered to and through the manifold member 110 may help to remove any exudate and other fluids from the wound 102 as well as any free-floating or dislodged portions 136 of necrotic tissue 124. As such, the reduced-pressure treatment system 100 may improve healing of the tissue site 101, e.g., wound 102. Further, in one embodiment, after one of the pincers 126 has been moved to a closed position and with continued delivery of reduced pressure and continued contraction of the manifold member 110, each pincer blade 130 may move from a closed position to a collapsed position whereby the inner surface 134 of each pincer blade 130 confronts or approaches the tissue-facing surface 120 of the manifold member 110 or folds on itself or the adjacent pincer 126.

Referring again primarily to FIG. 3, if the manifold member 110 is used with a secondary manifold 201 associated with but not coupled to the manifold member 110, the secondary manifold 201 may be placed proximate the tissue site 101 with pincers 126 abutting the tissue. Then, the manifold member 110 may be placed proximate the secondary manifold 201. The operation may then proceed analogously to that described above.

Figure 4:
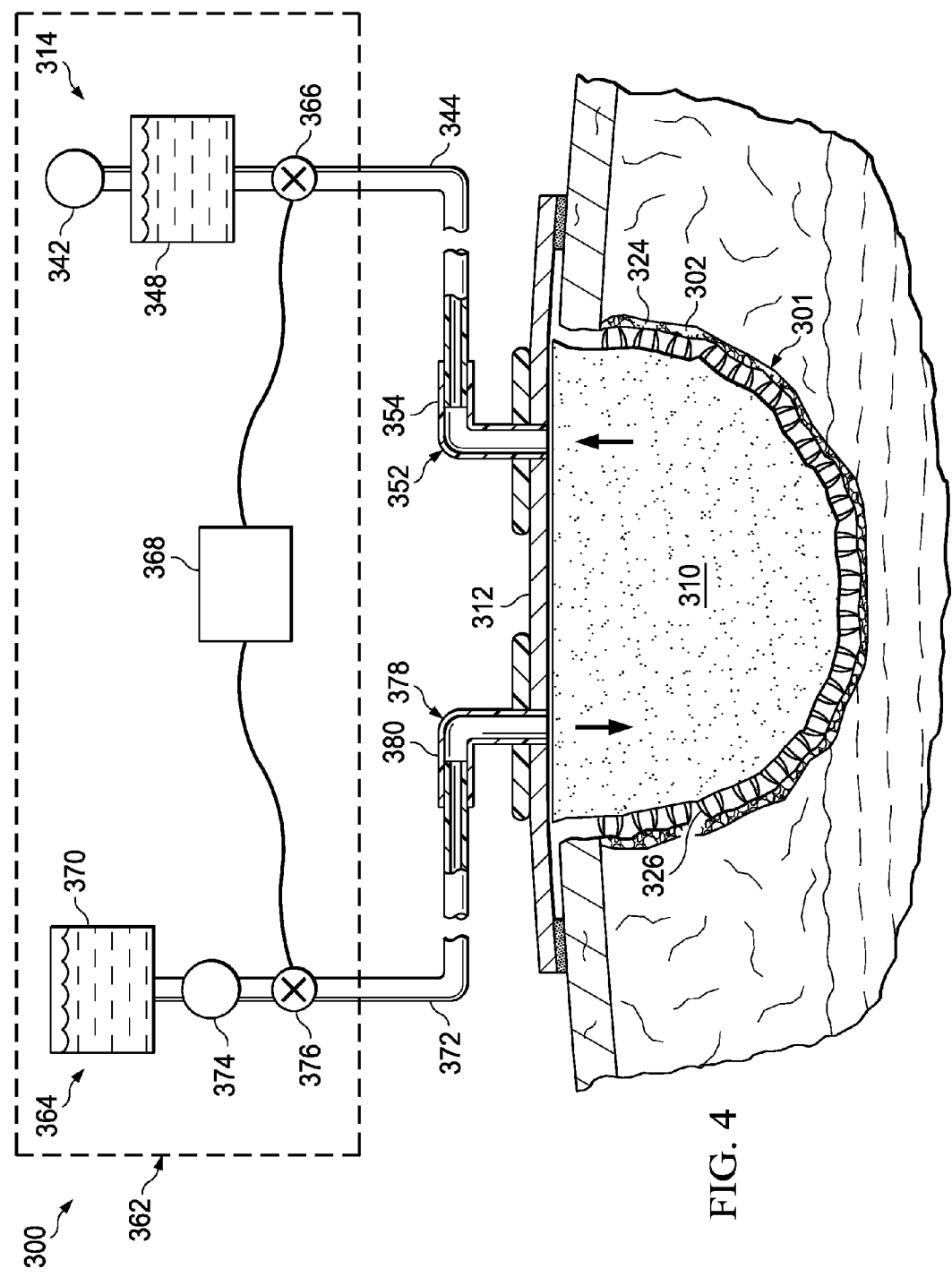
FIG. 4 is a schematic diagram with a portion shown in cross section of another illustrative, non-limiting embodiment of a reduced-pressure treatment system employing a debridement mechanism.

Referring now primarily to FIG. 4, another illustrative, non-limiting embodiment of a reduced-pressure treatment system 300 is shown for treating a tissue site 301, such as a wound 302. The reduced-pressure treatment system 300 is analogous in most respects to the reduced-pressure treatment system 100 of FIGS. 1-2C and a correlation of parts is generally indicated in this embodiment by indexing the numerals in FIGS. 1-2C by 200.

The reduced-pressure treatment system 300 further includes a fluid-management subsystem 362. The fluid-management subsystem 362 includes a reduced-pressure subsystem 314 and a chemical-debridement subsystem 364. The reduced-pressure subsystem 314 is similar, or the same, as the reduced-pressure subsystem 114 of FIG. 1.

The reduced-pressure subsystem 314 includes a reduced-pressure source 342 for delivering a reduced pressure. The reduced-pressure subsystem 314 may also include a canister 348 for receiving exudate, portions of tissue, debriding chemical(s), etc. that may be drawn from the interior portion of the sealing drape 312, tissue site 301, or manifold member 310. As will be discussed further below, delivery of the reduced pressure may be controlled by a controller 368 via a valve member 366. Alternatively or in addition, any suitable operator, such as a nurse, doctor or patient, may manually operate the valve member 366 to control delivery of the reduced pressure. The valve member 366 may be any suitable device operable to control the delivery of reduced pressure from the reduced-pressure source 342 to the interior of the sealing drape 312 and manifold member 310. Suitable valve members 366 include, without limitation, a clamp, stop valve, or check valve.

The reduced pressure developed by reduced-pressure source 342 is delivered through the reduced-pressure conduit 344 to a reduced-pressure interface 352, or interface 352, which may be an elbow port 354. Exudate, portions of tissue, debriding chemical(s), etc. may be drawn from the interior portion of the sealing drape 312, tissue site 301 (e.g., wound 302), or manifold member 310 and delivered to the canister 348 via the interface 352 and reduced-pressure conduit 344.

The chemical-debridement subsystem 364 includes a debriding chemical reservoir 370 in fluid communication with the interior portion of the sealing drape 312. The debriding chemical reservoir 370 may be placed in fluid communication with the interior portion of the sealing drape 312 via a second conduit 372 and a second interface 378, such as an elbow port 380. The debriding chemical reservoir 370 contains a debriding chemical that is capable of softening, digesting, partially digesting, breaking down or partially breaking down undesirable tissue, e.g., necrotic tissue 324, at the tissue site 301, e.g., the wound 302. Illustrative debriding chemicals, include, without limitation, collagenase, ficin, pepsin, trypsin, chymotrypsin, papain and elastase. Alternatively or in addition, the debriding chemical may be one or more enzymes, or one or more analogues thereof, isolated from any suitable insect larvae. In one embodiment, the larvae are larvae from *Lucilia sericata*; however, it will be appreciated that any suitable insect larvae may be employed. In one aspect, the debriding chemical is operable to soften digest, partially digest, break down or partially break down undesirable tissue at the tissue site 301 while leaving the healthy tissue at the tissue site 301 intact.

A pump 374 may be operable to deliver the debriding chemical from the debriding chemical reservoir 370 to the interior portion of the sealing drape 312. Alternatively or in addition, the debriding chemical may be delivered from the debriding chemical reservoir 370 to the interior portion of the sealing drape 312 via gravity or pulled by operation of the reduced-pressure subsystem 314. In either case, delivery of the debriding chemical may be controlled by the controller 368 via a second valve member 376. Alternatively or in addition, any suitable operator, such as a nurse, doctor or patient, may manually operate the second valve member 376 to control delivery of the debriding chemical. The second valve member 376 may be any suitable device operable to control the delivery of the debriding chemical reservoir 370 to the interior of the sealing drape 312 and manifold member 310.

Suitable second valve members 376 include, without limitation, a clamp, stop valve, or check valve.

While the illustrative, non-limiting embodiment employs a reduced-pressure conduit 344 and a second conduit 372, a single conduit may be employed for delivering both reduced pressure and the debriding chemical to the interior of the sealing drape 312 wherein the installation subsystem is configured to cycle between a debriding chemical delivery mode and a reduced-pressure mode. Moreover, in one embodiment, the fluid-management subsystem may include the V.A.C.® Instill® System developed by Kinetic Concepts, Inc. of San Antonio, Tex.

In operation of the reduced-pressure treatment system 300, the manifold member 310 and reduced-pressure subsystem 314 are arranged and installed as previously discussed in connection with the reduced-pressure treatment system 100 of FIG. 1. The second interface 378 may be applied, if not already installed, and the second conduit 372 fluidly coupled to the second interface 378. The second conduit 372 is also fluidly coupled to the pump 374, or debriding-chemical reservoir 370 if the debriding chemical is delivered via gravity or operation of the reduced-pressure subsystem 314.

The chemical-debridement subsystem 364 is operable to deliver a debriding chemical to the interior of the sealing drape 312 by the opening of, or partially opening of, the second valve member 376. The second valve member 376 may be operated by the controller 368 or any suitable operator. A pump 374, gravity, or operation of the reduced-pressure subsystem 314 may be utilized to move a debriding chemical from the debriding-chemical reservoir 370 to the interior of the sealing drape 312 and to the tissue site 301. The debriding chemical is operable to soften digest, partially digest, break down or partially break down undesirable tissue, e.g., necrotic tissue 324, at the tissue site 301, e.g., wound 302.

The reduced-pressure subsystem 314 is delivers reduced pressure to the interior of the sealing drape 312 by the opening of, or partial opening of, the valve member 366. The valve member 366 may be operated by the controller 368 or any suitable operator. In one embodiment, the opening, or partial opening, of the valve member 366 coincides with a closure, or partial closure, of the second valve member 376 whereby delivery of the debriding chemical ceases whilst a reduced-pressure is delivered to the interior of the sealing drape 312. The reduced-pressure subsystem 314 may be operated to remove fluids at a first pressure, followed by an increase in reduced-pressure so as to remove unwanted tissue; alternatively, the removal of fluids and unwanted tissue may be done with one operation.

Delivery of a reduced pressure may cause the pincers 326 to operate as previously discussed in connection with FIG. 1-2C, whereby the pincers 326 remove the softened digested, partially digested, broken down or partially broken down undesirable tissue, e.g., necrotic tissue 324, from the tissue site, e.g., wound 302. The reduced-pressure subsystem 314 may also be operable to draw exudate, portions of necrotic tissue, debriding chemical(s), etc. from the interior of the sealing drape 312 for receipt by the canister 348. Moreover, in one embodiment, the reduced-pressure subsystem 314 may also be operable to draw the debriding chemical from the debriding-chemical reservoir 370 to the interior of the sealing drape 312 for the delivery thereof.

The reduced-pressure treatment system 300 may be operated in a cyclical manner whereby a debriding chemical is delivered to the interior of the sealing drape 312, followed by a delivery of a reduced pressure and debridement by the pincers 326, which is, in turn, followed by a second delivery of a debriding chemical, and then, a second delivery of a reduce pressure and debridement by the pincers 326, etc.

In an alternative embodiment, the chemical-debridement subsystem 364 may include the debriding-chemical reservoir 370 that is in fluid communication with the reduced-pressure conduit 344 and a two-way valve may control when debridement chemical is delivered to the interface 352 and when reduced pressure is delivered from the reduced-pressure source 342. In this embodiment of the chemical-debridement subsystem 364, delivery is alternated between debridement chemical and reduced pressure to allow a single interface to be used.

Figure 5A:
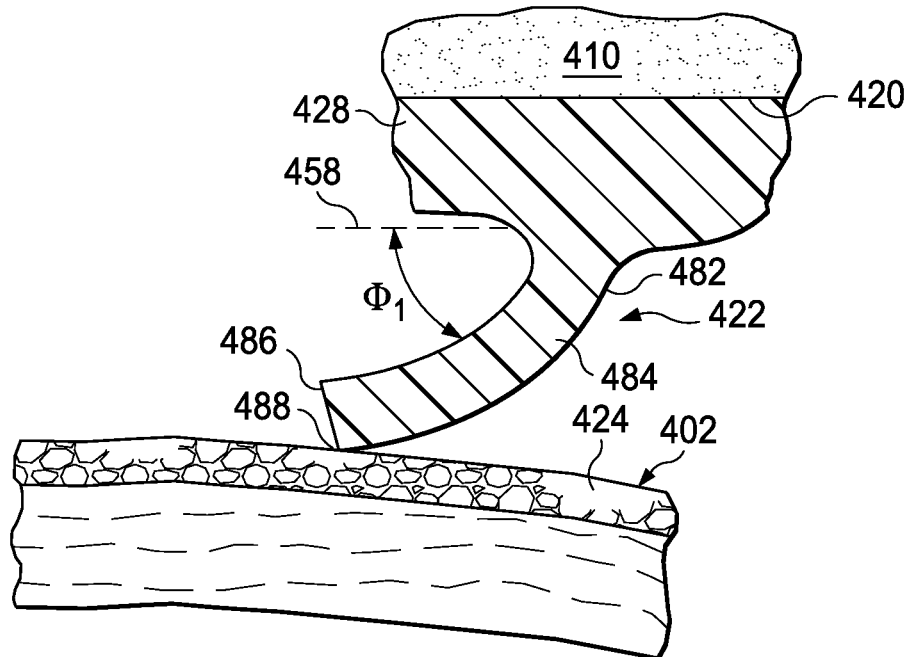
FIG. 5A is a schematic, cross-sectional view of an illustrative, non-limiting embodiment of a debridement implement, which is shown in a first position, for use as part of a reduced-pressure treatment system employing a debridement mechanism.
Figure 5B:
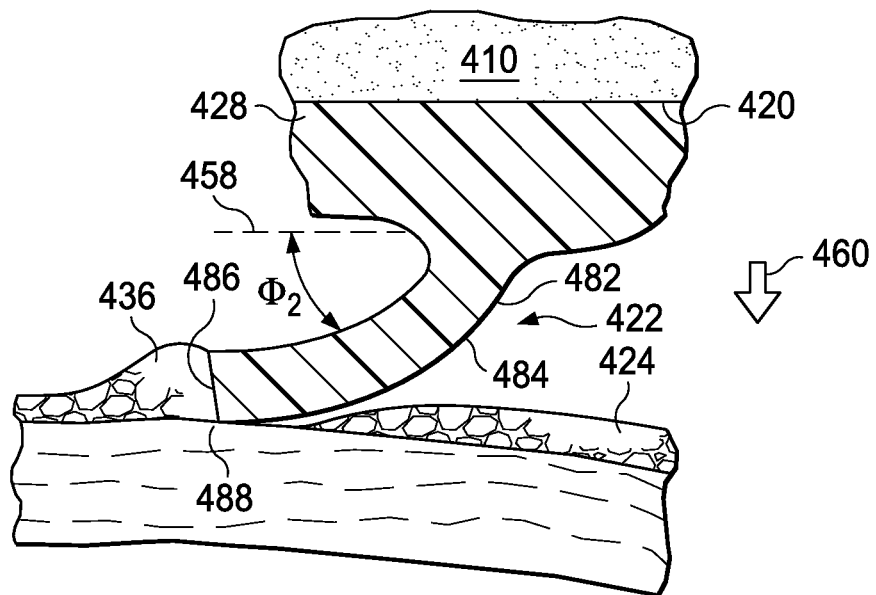
FIG. 5B is a schematic, cross-sectional view of the debridement implement of FIG. 5A shown in a second position.

Referring now primarily to FIGS. 5A and 5B, an alternative debridement mechanism 422 for use with a reduced-pressure pressure treatment system, such as reduced-pressure treatment systems 100, 300 (FIGS. 1-4), is shown. The debridement mechanism 422 includes a debridement implement 482, which may take numerous shapes and sizes to help remove tissue. The manifold member 410 may include any suitable number of debridement implements 482. In one embodiment, a plurality of debridement implements 482 is arranged in an array over the tissue-facing surface 420 of the manifold member 410. Alternatively, the manifold member 410 may include both one or more debridement implements 482 as well as one or more pincers 126 (FIGS. 1-4).

Each debridement implement 482 includes a debridement arm 484 with a face 486 at the distal end thereof. The proximal end of the debridement arm 484 may be integral with, or otherwise coupled to, a support member 428. The support member 428 may be integral with, or otherwise coupled to, or associated with the manifold member 410. The debridement implement 482 may extend from the manifold member 410 at any suitable angle. The debridement arm 484 has a distal end that is operable to engage undesired tissue.

The debridement arm 484 deforms under reduced pressure. The debridement implement 482 may be operable to move from a first, or neutral, position, with a first angle ($\Phi_1$) between the debridement arm 484 and a horizontal (for the orientation shown) reference line 458, to a second, or debriding, position with a second angle ($\Phi_2$) between the debridement arm 484 and the horizontal reference line 458. In one embodiment, the second angle is less than the first angle ($\Phi_2 < \Phi_1$). In another illustrative, non-limiting embodiment, a debridement mechanism includes a debridement utensil operable to remove undesired tissue through direct action against the tissue of the collapsible debridement utensil. The debridement utensil deforms under the influence of reduced pressure to remove the undesired tissue.

In operation according to one illustrative, non-limiting embodiment, the manifold member 410 is placed proximate a tissue site, e.g., wound 402, such that the edge 488 of the debridement face 486 abuts a portion of the tissue within the wound, e.g., necrotic tissue 424 (FIG. 5A). A sealing drape and reduced-pressure subsystem or fluid-management subsystem may be applied and activated as previously discussed. As reduced pressure is delivered, the manifold member 410 may contract to form a semi-rigid substrate. As reduced pressure is delivered and the manifold member 410 begins to contract, a compressive force develops in the direction represented by vector 460, which begins to drive the edge 488 of the face 486 into the necrotic tissue 424 thereby moving the debridement implement 482 from a first, or neutral, position to a second, or debriding, position. As the debridement implement 482 is moved to the second, or debriding, position, a portion 436 of necrotic tissue 424 may be forced by the face 486 from the wound 402 (FIG. 5B).

In an alternative embodiment, the manifold member 410 may be sized smaller than the tissue site to be treated whereby cyclical application of reduced pressure causes each face 486 to "push off" of the immediate portion 436 of necrotic tissue 424 removed such that the debridement implement "steps" to a second portion of necrotic tissue 424 whereby the manifold member 410 "moves" across the wound 402. In other words, each cycle of reduced pressure causes the manifold member 410 to advance laterally by one "step."

The systems and methods described above may be employed in numerous ways and another general, illustrative method of treating a wound will now be described. The method may be employed by any one of the previously discussed reduced-pressure treatment systems 100, 300 of FIGS. 1-5B, or by any other suitable device or means. The method may be a logic that is programmed into, or otherwise followed by, a controller, such as the controller 368 of FIG. 4. Alternatively, the method may be employed by any suitable operator, such as a doctor, nurse, or patient. First, a debriding chemical is introduced to a tissue site, e.g., a wound, having at least a portion of undesirable tissue for removal, e.g., necrotic tissue. The debriding chemical may be any chemical suitable for softening, digesting, partially digesting, breaking down or partially breaking down undesirable tissue at the tissue site. Illustrative debriding chemicals, include, without limitation, collagenase, ficin, pepsin, trypsin, chymotrypsin, papain, elastase, enzymes isolated isolated from any suitable insect larvae, or one or more analogues thereof.

The debriding chemical may be held at the tissue site for a prescribed amount of time thereby allowing the debriding chemical to soften, digest, partially digest, break down or partially break down undesirable tissue at the tissue site. A reduced pressure may then be applied to the tissue site whereby one or more debridement mechanisms debride the tissue site. The application of a reduced pressure to the tissue site may also serve to remove, or partially remove, exudate, the debriding chemical, free floating portions of undesirable tissue, etc. from the tissue site. Additionally, in one embodiment, the application of a reduced pressure to the tissue site is done in a cyclical manner; for example, the pressure may cycle between a first pressure at first pressure level and a second pressure at a second pressure level. The cycling may occur for a plurality of cycles.

After the application of a reduced pressure to the tissue site, a subsequent introduction of a debriding chemical to the tissue site may be performed. The subsequent introduction of a debriding chemical to the tissue site may serve to flush free floating portions of undesirable tissue from the tissue site as well as introduce a fresh batch of the debriding chemical to the tissue site for a subsequent softening, digesting, partially digesting, breaking down or partially breaking down of undesirable tissue at the tissue site. The debriding chemical may then be held at the tissue site for a prescribed amount of time and the process repeated. Alternatively or in addition, the tissue site may be flushed with a flushing agent, such as saline or any other medically acceptable fluid or solution, prior to a subsequent introduction of the debriding chemical or after a final debridement by the debridement mechanism.

Although the present invention and its advantages have been disclosed in the context of certain illustrative, non-limiting embodiments, it should be understood that various changes, substitutions, and alterations can be made without departing from the scope of the invention as defined by the appended claims.

We claim:

1. A reduced-pressure treatment system for treating a tissue site on a patient, the system comprising:
    a manifold member adapted to distribute reduced pressure to the tissue site and contract in response to application of reduced pressure to the tissue site;
    a support member mechanically coupled to the manifold member;
    a debridement mechanism having a proximal end coupled to the support member and a distal end having at least one cutting edge extending from and operatively coupled to the support member to debride the tissue site, wherein the debridement mechanism is deformable to drive the at least one edge against the undesired tissue in response to contraction of the manifold member when induced by the application of reduced pressure;
    a sealing drape for placing over the tissue site and manifold member and operable to form a fluid seal over the tissue site and manifold member;
    a source of reduced-pressure for delivering a reduced pressure through the sealing drape to the manifold member.

2. The system of claim 1, wherein the debridement mechanism comprises a pincer having a first blade and a second blade, each including one of the at least one cutting edges and being movable for debriding the tissue site in response to contraction of the manifold member.

3. The system of claim 2, wherein the first blade and the second blade of the pincer move from an open position to a closed position when the manifold member contracts under the influence of reduced pressure.

4. The system of claim 1, wherein the debridement mechanism comprises a debridement arm having a cutting edge movable for debriding the tissue site in response to contraction of the manifold member.

5. The system of claim 4, wherein the debridement arm deforms to move from a first position to a second position when the manifold member by moving the cutting edge from a first position to a second position.

6. The system of claim 1, further comprising a chemical-debridement subsystem for delivering a debriding chemical to the tissue site.

7. The system of claim 1, further comprising a chemical-debridement subsystem for delivering a debriding chemical to the tissue site, wherein the chemical-debridement subsystem comprises a debriding chemical reservoir in fluid communication with the sealing drape whereby the debriding chemical is delivered to the tissue site.

8. The system of claim 1, further comprising a chemical-debridement subsystem for delivering a debriding chemical to the tissue site, wherein the debriding chemical is one or more enzymes isolated from insect larvae.

9. The system of claim 1, further comprising a chemical-debridement subsystem for delivering a debriding chemical to the tissue site, wherein the debriding chemical is one or more enzymes isolated from insect larvae, and wherein the larvae are larvae from *Lucilia sericata*.

10. The system of claim 1, further comprising a chemical-debridement subsystem for delivering a debriding chemical to the tissue site, wherein the debriding chemical is one or more synthetic analogues of one or more enzymes isolated from insect larvae.

11. The system of claim 1, further comprising a chemical-debridement subsystem for delivering a debriding chemical to the tissue site, wherein the debriding chemical is one or more synthetic analogues of one or more enzymes isolated from insect larvae, and wherein the larvae are larvae from *Lucilia sericata*.

12. The system of claim 1, further comprising a chemical-debridement subsystem for delivering a debriding chemical to the tissue site, wherein the debriding chemical is a chemical selected from the group consisting of: collagenase, ficin, pepsin, trypsin, chymotrypsin, papain and elastase.

13. The system of claim 1, wherein the debridement mechanism comprises a jaw formed by two of the at least one blade including a first jaw member and a second jaw member,
wherein the first jaw member and second jaw member are operable to move from a first, open position to a second, biting position under the influence of reduced pressure.

14. A manifold member for treating a tissue site on a patient, the manifold member comprising:
a manifold material adapted to distribute reduced pressure to the tissue site and contract in response to application of reduced pressure and distribute reduced pressure to the tissue site;
a support member mechanically coupled to the manifold material; and
a debridement mechanism having a proximal end coupled to the support member and a distal end having at least one cutting edge extending from and operatively coupled to the support member to debride the tissue site, wherein the debridement mechanism is deformable to drive the at least one cutting edge against the undesired tissue in response to contraction of the manifold material when induced by the application of reduced pressure.

15. The manifold member of claim 14, wherein the debridement mechanism comprises a pincer having a first blade and a second blade, each including one of the at least one cutting edges and being movable for debriding the tissue site in response to contraction of the manifold member.

16. The manifold member of claim 15, wherein the first blade and the second blade of the pincer move from an open position to a closed position under the influence of reduced pressure.

17. The manifold member of claim 15, wherein the first blade and the second blade of the pincer move from an open position to a closed position under the influence of reduced pressure, and wherein the first blade and the second blade of the pincer move from a closed position to a collapsed position under the influence of additional reduced pressure.

* * * * *